United States Patent
Yoo et al.

(10) Patent No.: US 10,945,603 B2
(45) Date of Patent: Mar. 16, 2021

(54) DETECTING POTENTIAL HEALTH RISKS USING NANOROBOTICS

(71) Applicant: AT&T Intellectual Property I, L.P., Atlanta, GA (US)

(72) Inventors: Brian Yoo, Mount Tabor, NJ (US); Victoria Rinaldi, Freehold, NJ (US); Harish Venkata Kajur, Piscataway, NJ (US); Ronald Sedlak, Ocean Grove, NJ (US)

(73) Assignee: AT&T INTELLECTUAL PROPERTY I, L.P., Atlanta, GA (US)

( * ) Notice: Subject to any disclaimer, the term of this patent is extended or adjusted under 35 U.S.C. 154(b) by 467 days.

(21) Appl. No.: 15/463,260

(22) Filed: Mar. 20, 2017

(65) Prior Publication Data

US 2018/0263494 A1     Sep. 20, 2018

(51) Int. Cl.
*A61B 5/00*     (2006.01)
*A61B 5/07*     (2006.01)
(Continued)

(52) U.S. Cl.
CPC ............ *A61B 5/0022* (2013.01); *A61B 5/073* (2013.01); *A61B 5/14546* (2013.01); *A61B 5/746* (2013.01); *G01N 27/3278* (2013.01); *A61B 5/1473* (2013.01); *A61B 5/411* (2013.01); *A61B 5/4839* (2013.01); *A61B 5/6846* (2013.01);
(Continued)

(58) Field of Classification Search
CPC .......... B82Y 5/00; B82Y 10/00; B82Y 15/00; B81B 2201/0214; G06N 3/002; A61B 5/1473; A61B 5/411; A61B 5/4839; A61B 5/14546; A61B 2560/0214; A61B 2560/028; A61B 2562/0285; G01N 27/3278
See application file for complete search history.

(56) References Cited

U.S. PATENT DOCUMENTS

| 6,632,175 B1 | 10/2003 | Marshall |
| 7,354,433 B2 | 4/2008 | Pierce |

(Continued)

FOREIGN PATENT DOCUMENTS

| JP | 2016014074 A | 1/2016 |
| KR | 20110016004 A | 2/2011 |
| WO | 2008063473 A2 | 10/2008 |

OTHER PUBLICATIONS

Cavalcanti, A., Shirinzadeh, B., & Kretly, L. C. (2008). Medical nanorobotics for diabetes control. Nanomedicine: Nanotechnology, Biology and Medicine, 4(2), 127-138. (Year: 2008).*

(Continued)

*Primary Examiner* — Devin B Henson (57) ABSTRACT

In one example, a device includes a detector, a sensor, a transceiver, and a reservoir. The detector triggers a chemical reaction upon contact with a target substance in a user's body. The sensor detects when the chemical reaction occurs. The transceiver transmits a first electronic signal containing a record of the chemical reaction to a user endpoint device for use in detecting potential health risks and receives a second electronic signal containing an instruction to dispense, from the reservoir, a medication for treating a condition indicated by a presence of the target substance in the user's body from the user endpoint device.

20 Claims, 5 Drawing Sheets

(51) Int. Cl.
G01N 27/327 (2006.01)
A61B 5/145 (2006.01)
A61B 5/1473 (2006.01)

(52) U.S. Cl.
CPC ......... A61B 5/742 (2013.01); A61B 2560/028 (2013.01); A61B 2560/0214 (2013.01); A61B 2562/0285 (2013.01); A61M 2250/00 (2013.01)

(56) References Cited

U.S. PATENT DOCUMENTS

| | | | |
|---|---|---|---|
| 7,399,400 B2* | 7/2008 | Soundarrajan ......... | B82Y 10/00 204/403.01 |
| 8,200,310 B2 | 6/2012 | Jonckheere et al. | |
| 8,236,243 B2 | 8/2012 | Palena et al. | |
| 8,497,777 B2* | 7/2013 | Harper ................... | G06F 19/00 340/573.1 |
| 8,597,278 B2 | 12/2013 | Trovato | |
| 8,634,969 B2 | 1/2014 | Buelthoff et al. | |
| 8,768,501 B2 | 7/2014 | Fischer et al. | |
| 9,067,047 B2* | 6/2015 | Wood, Jr. ............. | A61B 5/4839 |
| 9,393,396 B2 | 7/2016 | Peyman | |
| 9,451,899 B2 | 9/2016 | Ritchey et al. | |
| 2005/0208121 A1 | 9/2005 | Barton et al. | |
| 2006/0252143 A1* | 11/2006 | Lo ...................... | A61B 5/04001 435/287.1 |
| 2008/0241065 A1 | 10/2008 | Benaron et al. | |
| 2008/0241264 A1 | 10/2008 | Solomon | |
| 2008/0243303 A1 | 10/2008 | Solomon | |
| 2009/0214474 A1 | 8/2009 | Jennings | |
| 2010/0132469 A1 | 6/2010 | Giurgiutiu et al. | |
| 2010/0204676 A1 | 8/2010 | Cardullo | |
| 2010/0303716 A1* | 12/2010 | Jin .................... | A61M 37/0092 424/1.11 |
| 2011/0048433 A1 | 3/2011 | Pfister | |
| 2012/0072230 A1 | 3/2012 | Jape et al. | |
| 2012/0209088 A1 | 8/2012 | Romem | |
| 2014/0218537 A1 | 8/2014 | Nepo | |
| 2015/0184213 A1 | 7/2015 | Elbaz et al. | |
| 2015/0265743 A1 | 9/2015 | Hanson et al. | |
| 2015/0343144 A1* | 12/2015 | Altschul ............. | A61K 9/0097 604/503 |
| 2016/0189174 A1 | 6/2016 | Heath | |
| 2017/0087299 A1* | 3/2017 | Anderson .......... | A61B 5/14546 |
| 2018/0103879 A1* | 4/2018 | Masciotti ............. | A61B 5/0024 |

OTHER PUBLICATIONS

Huang, W., Wang, G., Lu, J., Gao, F., Qiao, Z., & Sun, L. (Aug. 2013). Thermoelectric generator device based on carbon nanotube membrane. In 2013 13th IEEE International Conference on Nanotechnology (IEEE-NANO 2013) (pp. 946-949). IEEE. (Year: 2013).*
Ou, H. C., & Szu, H. (Apr. 2006). Designs of solar voltaic cells based on carbon nano-tubes. In Independent Component Analyses, Wavelets, Unsupervised Smart Sensors, and Neural Networks IV (vol. 6247, p. 62470F). International Society for Optics and Photonics. (Year: 2006).*
Robert, A. F. J. (2009). Medical Nanorobotics: The Long-Term Goal for Nanomedicine. Nanomedicine Design of Particles, Sensors, Motors, Implants, Robots, and Devices, Artech House, Norwood MA, 367-392. (Year: 2009).*
Cavalcanti, A., Shirinzadeh, B., Freitas, R. A., & Kretly, L. C. (2007). Medical nanorobot architecture based on nanobioelectronics. Recent Patents on Nanotechnology, 1(1), 1-10. (Year: 2007).*
Wang, Z. L. (2008). Energy harvesting for self-powered nanosystems. Nano Research, 1(1), 1-8. (Year: 2008).*
Endo, Hideaki, et al, "Wireless enzyme sensor system for real-time monitoring of blood glucose levels in fish", Biosensors and Bioelectronics, pp. 1417-1423, Sep. 2, 2008, Elsevier B.V.
Gao, Wei et al., "Fully integrated wearable sensor arrays for multiplexed in situ perspiration analysis", Nature, pp. 509-526, Jan. 28, 2016, Macmillan Publishers Ltd.
DeHennis, Andrew et al., "An NFC-Enabled CMOS IC for a Wireless Fully Implantable Glucose Sensor", IEEE Journal of Biomedical and Health Informatics, Sep. 2015 (doi: 10.1109/JBHI.2015.2475238), IEEE.
Chiu, Nan-Fu et al., "An Implantable Multifunctional Needle Type Biosensor with Integrated RF Capability," Proceedings of the 2015 IEEE Engineering in Medicine and Biology $27^{th}$ Annual Conference, pp. 1933-1936, Sep. 2015.
U.S. Food and Drug Administration, "What is the pancreas? What is an artificial pancreas device system?" webpage versions as edited Sep. 28, 2016. Retrieved from Internet Archive Wayback capture from Jan. 12, 2019.
Freitas Jr., Robert, "Nanomedicine, vol. 1: Basic Capabilities", pp. 93-97, 182-183, 189, 191-192, 197-206, 359-367, 1999, Landes Bioscience, Austin, TX.
Christiansen, Mark et al., "A New, Wireless-enabled Blood Glucose Monitoring System That Links to a Smart Mobile Device: Accuracy and User Performance Evaluation", Journal of Diabetes Science and Technology, 2017, vol. 1(3), pp. 567-573.
Hanazaki, Kazuhiro et al., "Current topics in glycemic control by wearable artificial pancreas or bedside artificial pancreas with closed-loop system", Journal of Artificial Organs, published online May 3, 2016 (doi 10.1007/s10047-016-0904-y).
M. Sivasankar et al., "Brief review on nano robots in bio medical applications." Adv. Robot. Autom. vol. 1 Issue 1 (Feb. 27, 2012). pp. 1-4. https://www.omicsgroup.org/journals/brief-review-on-nano-robots-in-bio-medical-applications-2168-96 95.1000101.pdf.
Adriano Cavalcanti et al., "Nanorobot hardware architecture for medical defense." Sensors vol. 8 Issue 5 (May 6, 2008). pp. 2932-2958. http://www.mdpi.org/sensors/papers/s8052932.pdf.
Pao Chang, "Nanotechnology in Medicine: Using Nanobots to Treat Cancer and Disease." Energy Fanatics, energyfanatics.com (Apr. 24, 2014). 7 Pages. http://energyfanatics.com/2014/04/24/nanotechnology-medicine-using-nanobots-treat-cancer-disease/.
"South Korean Scientists Develop the World's First CancerTreating Nanorobots." Innovate Medtec, innovatemedtec.com, Jun. 2, 2014. 6 Pages https://innovatemedtec.com/content/nanorobots.
Adriano Cavalcanti et al., "Nanorobot architecture for medical target identification." Nanotechnology vol. 19 No. 1 (Nov. 29, 2007). 15 Pages. http://citeseerx.ist.psu.edu/viewdoc/download?doi=10.1.1.692.7099&rep=rep1&type=pdf.
Robert A. Freitas, "Current status of nanomedicine and medical nanorobotics." Journal of Computational and Theoretical Nanoscience vol. 2 No. 1 ( Mar. 1, 2005). pp. 1-25. http://www.nanomedicine.com/Papers/NMRevMar05.pdf.

* cited by examiner

DETECTING POTENTIAL HEALTH RISKS USING NANOROBOTICS

The present disclosure relates generally to biomedical monitoring, and relates more particularly to devices, non-transitory computer-readable media, and methods for detecting health risks using nanorobotics.

BACKGROUND

Various systems exist for monitoring and/or treating biomedical conditions. For instance, there are home testing kits for monitoring conditions such as diabetes and high cholesterol. There are also reactive agents and devices that can detect when unwanted or unhealthy substances (e.g., drugs) have been introduced into a person's food or drink. There are also devices for administering medication in the event of a medical emergency, such as an allergic reaction or an injury.

SUMMARY

In one example, the present disclosure describes a device, computer-readable medium, and method for detecting potential health risks using nanorobotics. For instance, in one example, a device includes a detector, a sensor, and a transceiver. The detector triggers a chemical reaction upon contact with a target substance in a user's body. The sensor detects when the chemical reaction occurs. The transceiver transmits an electronic signal containing a record of the chemical reaction to a user endpoint device.

In another example, a method includes forwarding a first electronic signal received from a nanite deployed in a user's body to a remote server. The first electronic signal contains a record of a chemical reaction detected by the nanite in the user's body. The method further includes receiving a second electronic signal from the remote server. The second electronic signal contains an instruction for responding to a potential health risk indicated by the chemical reaction. The method further includes taking an action to mitigate the potential health risk based on the instruction.

In another example, a device includes a processor and a computer-readable medium storing instructions which, when executed by the processor, cause the processor to perform operations. The operations include forwarding a first electronic signal received from a nanite deployed in a user's body to a remote server. The first electronic signal contains a record of a chemical reaction detected by the nanite in the user's body. The operations further include receiving a second electronic signal from the remote server. The second electronic signal contains an instruction for responding to a potential health risk indicated by the chemical reaction. The operations further include taking an action to mitigate the potential health risk based on the instruction.

BRIEF DESCRIPTION OF THE DRAWINGS

The teachings of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

In one example, the present disclosure detects potential health risks using nanorobotics. As discussed above, various systems exist for monitoring and/or treating biomedical conditions, such as diabetes, high cholesterol, allergies, hemophilia, and exposure to unwanted and/or unhealthy substances, among other conditions. However, many of these systems are subject to false results due to equipment degradation and failure, contamination, human error, or other factors. Moreover, the response times of such systems may not be quick enough to allow treatment to be administered in a timely manner.

Examples of the present disclosure use ingestible, non-toxic nano-scale robotics (also referred to as "nanorobotics" or "nanites") to monitor biomedical conditions on an on-demand or continuous basis, and, in some cases, to administer treatments such as medications. The nanites include a detection mechanism, which may be chemical in nature, as well as short-range transceivers which allow them to communicate and to share data with nearby computing devices. In some examples, the nanites may further include a reservoir of medication and a dispensing mechanism for dispensing the medication.

Moreover, although the disclosure is primarily describes a context in which the end user is human, it will be appreciated that the nanites of the present disclosure could also be deployed to monitor potential health risks to non-human users, such as animals. Since animals cannot communicate verbally with humans, this can make it difficult to diagnose the conditions of their health. Deploying nanites into their systems or bodies may help to identify some of these conditions in a timely manner (e.g., to detect when a dog has consumed chocolate or a poisonous plant).

Figure 1:
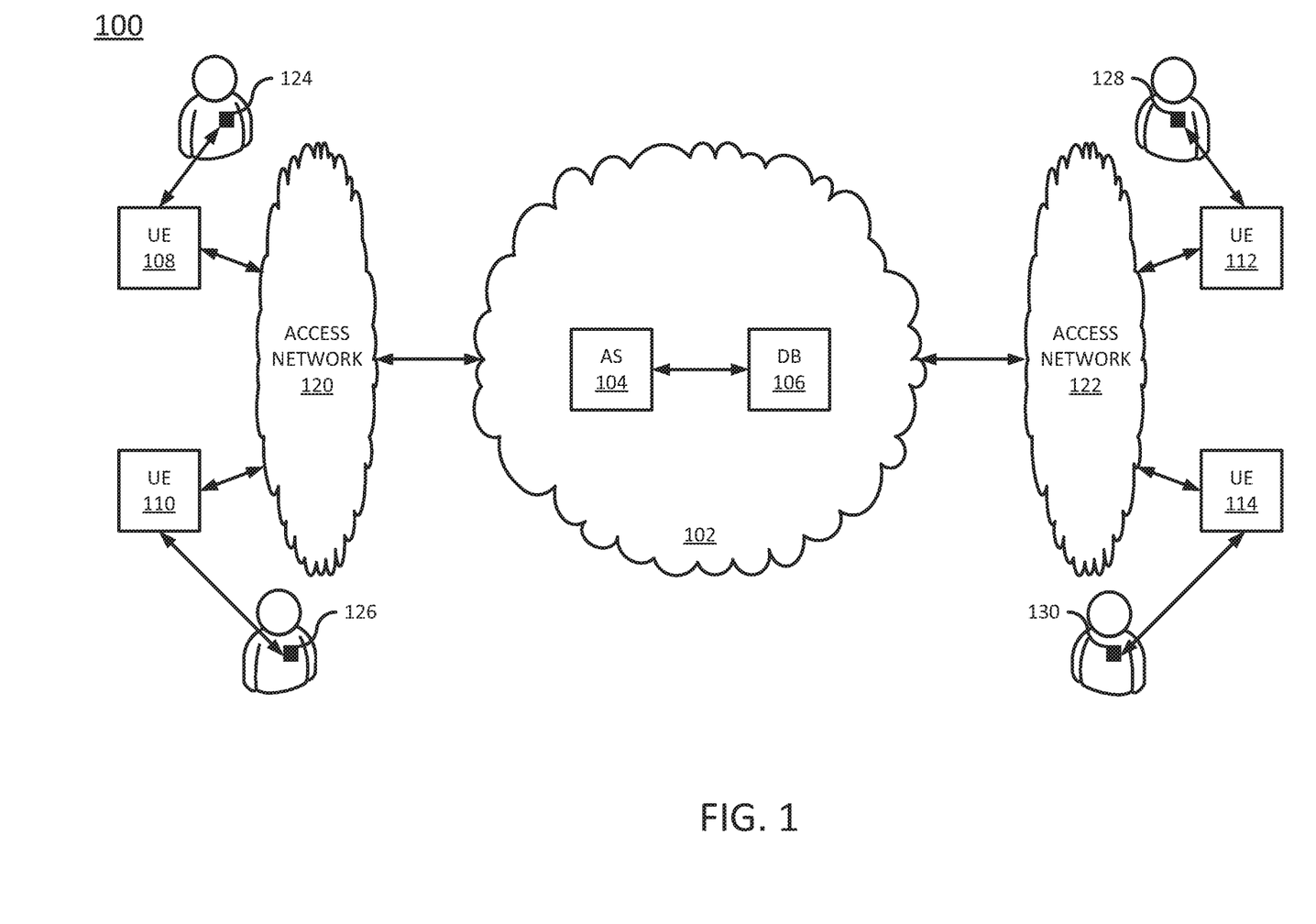
FIG. 1 illustrates an example network related to the present disclosure.

To better understand the present disclosure, FIG. 1 illustrates an example network 100, related to the present disclosure. The network 100 may be any type of communications network, such as for example, a traditional circuit switched network (CS) (e.g., a public switched telephone network (PSTN)) or an Internet Protocol (IP) network (e.g., an IP Multimedia Subsystem (IMS) network, an asynchronous transfer mode (ATM) network, a wireless network, a cellular network (e.g., 2G, 3G and the like), a long term evolution (LTE) network, and the like) related to the current disclosure. It should be noted that an IP network is broadly defined as a network that uses Internet Protocol to exchange data packets. Additional exemplary IP networks include Voice over IP (VoIP) networks, Service over IP (SoIP) networks, and the like.

In one example, the network 100 may comprise a core network 102. In one example, core network 102 may combine core network components of a cellular network with components of a triple play service network; where triple play services include telephone services, Internet services, and television services to subscribers. For example, core network 102 may functionally comprise a fixed mobile convergence (FMC) network, e.g., an IP Multimedia Subsystem (IMS) network. In addition, core network 102 may functionally comprise a telephony network, e.g., an Internet Protocol/Multi-Protocol Label Switching (IP/MPLS) backbone network utilizing Session Initiation Protocol (SIP) for circuit-switched and Voice over Internet Protocol (VoIP) telephony services. Core network 102 may also further comprise an Internet Service Provider (ISP) network. In one embodiment, the core network 102 may include an application server (AS) 104 and a database (DB) 106. Although only a single AS 104 and a single DB 106 are illustrated, it should be noted that any number of application servers 104 or databases 106 may be deployed. Furthermore, for ease of illustration, various additional elements of core network 102 are omitted from FIG. 1.

Figure 6:
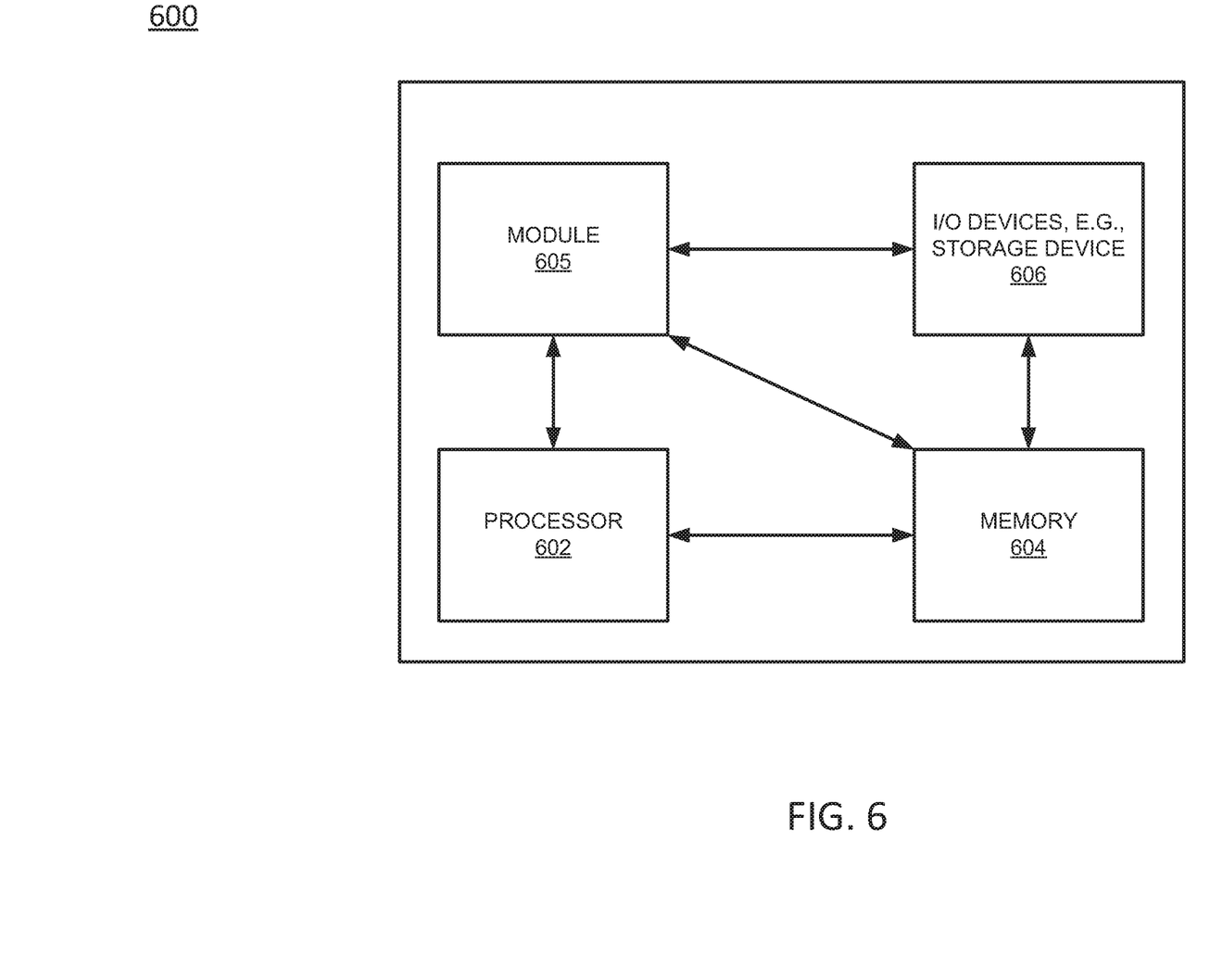
FIG. 6 depicts a high-level block diagram of a computing device specifically programmed to perform the functions described herein.

In one embodiment, the AS 104 may comprise a general purpose computer as illustrated in FIG. 6 and discussed below. In one embodiment, the AS 104 may perform the methods discussed below related to detecting potential health risks.

In one embodiment, the DB 106 may store data relating to user health. For example, the DB 106 may store user profiles, which users can update dynamically at any time. User profiles may include contact information (e.g., mobile phone number, email address, etc.) for the user and/or the user's healthcare provider(s). User profiles may also include user health history information (e.g., medications taken, allergies, known medical conditions, measurements of weight, blood pressure, or other health-related metrics, etc.). User profiles may also store data transmitted by nanites in the associated users' systems or bodies. User profiles may be stored in encrypted form to protect user privacy.

The core network 102 may be in communication with one or more wireless access networks 120 and 122. Either or both of the access networks 120 and 122 may include a radio access network implementing such technologies as: global system for mobile communication (GSM), e.g., a base station subsystem (BSS), or IS-95, a universal mobile telecommunications system (UMTS) network employing wideband code division multiple access (WCDMA), or a CDMA3000 network, among others. In other words, either or both of the access networks 120 and 122 may comprise an access network in accordance with any "second generation" (2G), "third generation" (3G), "fourth generation" (4G), Long Term Evolution (LTE), or any other yet to be developed future wireless/cellular network technology including "fifth generation" (5G) and further generations. The operator of core network 102 may provide a data service to subscribers via access networks 120 and 122. In one embodiment, the access networks 120 and 122 may all be different types of access networks, may all be the same type of access network, or some access networks may be the same type of access network and other may be different types of access networks. The core network 102 and the access networks 120 and 122 may be operated by different service providers, the same service provider or a combination thereof.

In one example, the access network 120 may be in communication with one or more user endpoint devices (also referred to as "endpoint devices" or "UE") 108 and 110, while the access network 122 may be in communication with one or more user endpoint devices 112 and 114. Access networks 120 and 122 may transmit and receive communications between respective UEs 108, 110, 112, and 114 and core network 102 relating to communications with web servers, AS 104, and/or other servers via the Internet and/or other networks, and so forth.

In one embodiment, the user endpoint devices 108, 110, 112, and 114 may be any type of subscriber/customer endpoint device configured for wireless communication such as a laptop computer, a Wi-Fi device, a Personal Digital Assistant (PDA), a mobile phone, a smartphone, an email device, a computing tablet, a messaging device, a wearable "smart" device (e.g., a smart watch or fitness tracker), a portable media device (e.g., an MP3 player), a gaming console, a portable gaming device, and the like. In one example, any one or more of the user endpoint devices 108, 110, 112, and 114 may have both cellular and non-cellular access capabilities and may further have wired communication and networking capabilities. It should be noted that although only four user endpoint devices are illustrated in FIG. 1, any number of user endpoint devices may be deployed.

Figure 2:
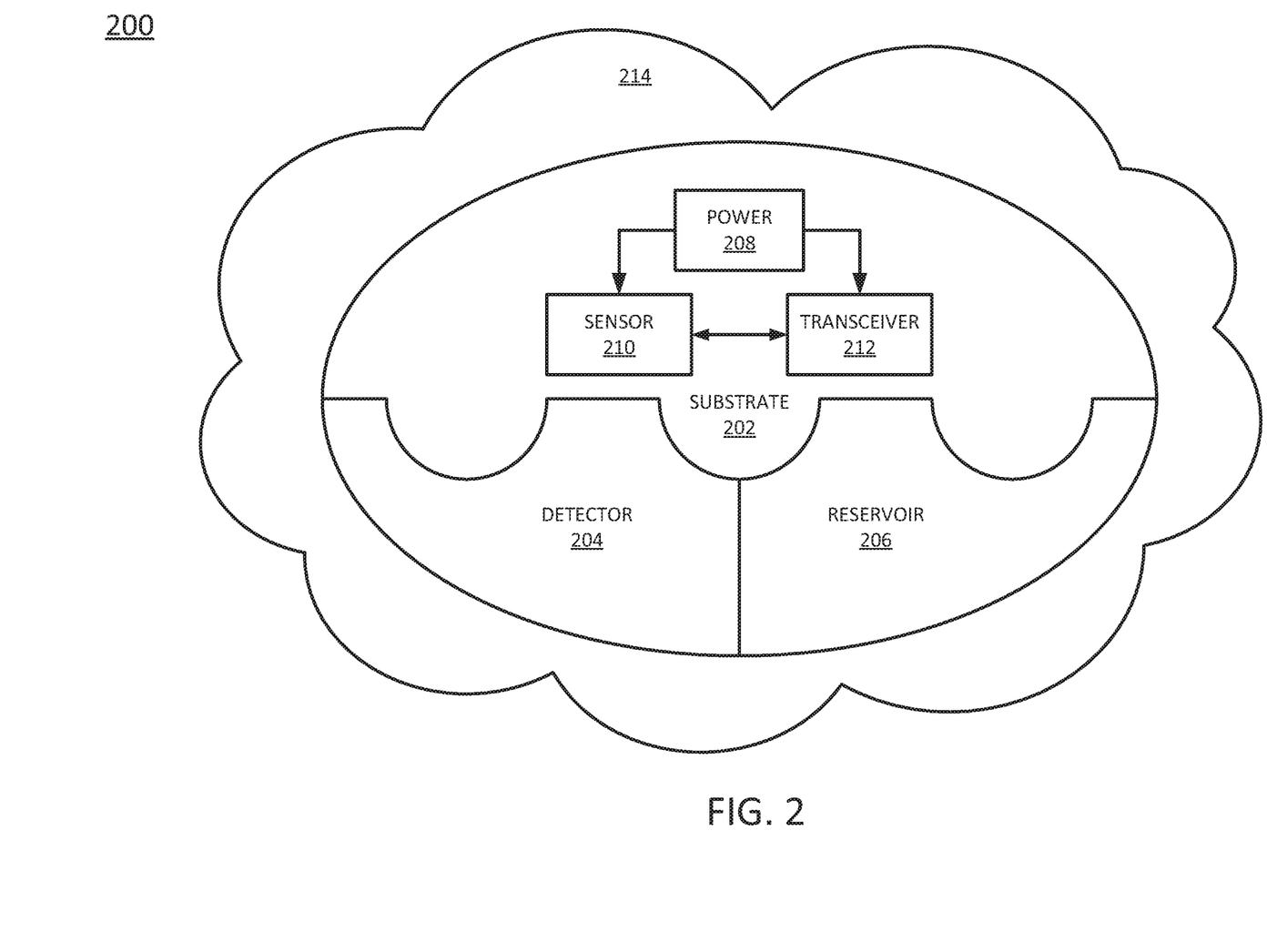
FIG. 2 illustrates an example of a nanite that may be used to detect a potential health risk.

In one example, the UEs 108, 110, 112, and 114 may be in further communication with one or more nanites 124, 126, 128, or 130 that have been ingested by a human user. Each of the nanites 124, 126, 128, or 130 may include a detection mechanism for detecting one or more biomedical conditions in the user. For instance, the detection mechanism may be non-toxic chemical that produces a reaction when it comes into contact with certain substances or antibodies. Each of the nanites 124, 126, 128, or 130 may also include a transceiver for communicating with the UEs 108, 110, 112, and 114 (e.g., over a near field communication protocol or other short range communication protocol). In some examples, the nanites may further include a reservoir of medication and a dispensing mechanism for dispending the medication. In one embodiment, the nanites 124, 126, 128, or 130 may be configured as illustrated in FIG. 2 and discussed below It should also be noted that as used herein, the terms "configure" and "reconfigure" may refer to programming or loading a computing device with computer-readable/computer-executable instructions, code, and/or programs, e.g., in a memory, which when executed by a processor of the computing device, may cause the computing device to perform various functions. Such terms may also encompass providing variables, data values, tables, objects, or other data structures or the like which may cause a computer device executing computer-readable instructions, code, and/or programs to function differently depending upon the values of the variables or other data structures that are provided. For example, any one or more of the user endpoint devices 108, 110, 112, and 114 may host an operating system for presenting a user interface that may be used to send data to the AS 104 (e.g., signals from nanites 124, 126, 128, or 130 or other data) and for reviewing data sent by the AS 104 (e.g., alerts, recommendations, etc.).

Those skilled in the art will realize that the network 100 has been simplified. For example, the network 100 may include other network elements (not shown) such as border elements, routers, switches, policy servers, security devices, a content distribution network (CDN) and the like. The network 100 may also be expanded by including additional endpoint devices, access networks, network elements, application servers, etc. without altering the scope of the present disclosure.

To further aid in understanding the present disclosure, FIG. 2 illustrates an example of a nanite that may be used to detect a potential health risk. Any of the nanites 124, 126, 128, or 130 of FIG. 1 may be configured to include the elements of the nanite 200 illustrated in FIG. 2. In one example, nanites configured as illustrated in FIG. 2 may be deployed to a user's system or body orally (e.g., by ingesting a pill or other comestible) or by injection. Nanites that are orally ingested may adhere to the inside of the user's mouth in order to detect substances as they enter the user's mouth. Nanites that are orally ingested or deployed via injection may make their way into the user's bloodstream in order to detect antibodies, pathogens, or other substances in the user's blood. Nanites may exit the user's body via the same natural processes that remove dead blood cells.

As illustrated in FIG. 2, the nanite 200 generally comprises a substrate 202, a detector 204, and a reservoir 206. The substrate 202 houses most of the non-consumable components of the nanite (e.g., power sources and circuitry), while the detector 204 and the reservoir 206 house consumable components that are used up in the detection and treatment of potential health risks. The substrate 202, detector 204, and reservoir 206 may be coupled together for ease of deployment and operation.

In one example, the detector 204 comprises a consumable substance that reacts with certain other substances in the user's system. For instance, the detector 204 may comprise a catalyst or enzyme that triggers a chemical reaction when it comes into contact with certain substances that may present or be indicative of an imminent health risk (e.g., drugs, allergens, antibodies, or pathogens. In one example, this chemical reaction exhausts the nanite's supply of the detector 204. The precise material composition of the detector 204 may be selected to react with a specific substance of interest (e.g., a target substance).

The reservoir 206 may contain a supply of medication or other substance used to treat certain health risks. For instance, the reservoir 204 may contain a supply of epinephrine to treat exposure of the user to an allergen, a supply of clotting factors used to treat a hemophiliac user who has sustained an open wound, or a supply of lactase to help a lactose-intolerant user's body break down lactose.

As discussed above, the substrate 202 houses most of the non-consumable components of the nanite 200. In one example, these components include a power source 208, a sensor 210, and a transceiver 212.

The power source 208 provides power (e.g., electrical power) to one or both of the sensor 210 and the transceiver 212. In one example, the power source 208 comprises a non-toxic battery that stores a limited amount of energy. In another example, the power source 208 comprises a non-toxic battery that stores converted energy from a renewable source. For instance, the battery may comprise a thermoelectric generator that converts the user's body heat into energy, or a photovoltaic cell that converts the sun's infrared radiation (absorbed by the user's skin) into energy. In a further example, a battery based on a thermoelectric generator may also be capable of regulating the user's body temperature if it can absorb enough heat.

The sensor 210 comprises a device that is capable of detecting chemical reactions within a limited spatial range. In particular, the sensor 210 detects chemical reactions triggered by the detector 204 coming into contact with certain substances in the user's system or body. The sensor 210 is further configured to send signals to the transceiver 212 when it detects such chemical reactions. In a further example, the sensor 210 is also able to detect when the nanite 200 is close to expiration (e.g., due to exhaustion of the detector 204 or the power source 208) and to send a signal to the transceiver 212 to alert it to the approaching expiration.

The transceiver 212 includes at least a transmitter for transmitting the signals sent by the sensor 210. In one example, the transmitter transmits the signals using a short range communication protocol, such as a near-field communication protocol. In a further example, the transceiver 212 may also include a receiver. The receiver may receive signals containing instructions, such as instructions to dispense medication from the reservoir 206.

In some examples, the nanite 200 may further include a small amount of local memory (not shown) that allows it to at least temporarily store signals from the detector 204 until they can be transmitted by the transceiver 212.

In one example, the nanite 200 may further comprise a shell 214 that at least temporarily encloses all or some of the substrate 202, the detector 204, and the reservoir 206. The shell 214 may have a structure that allows the nanite 200 to adhere to a surface, such as the flesh inside of a user's mouth. For instance, the shell 214 may take the shape of a spiked ball, where the spikes help the nanite 200 to adhere to the surface.

Figure 3:
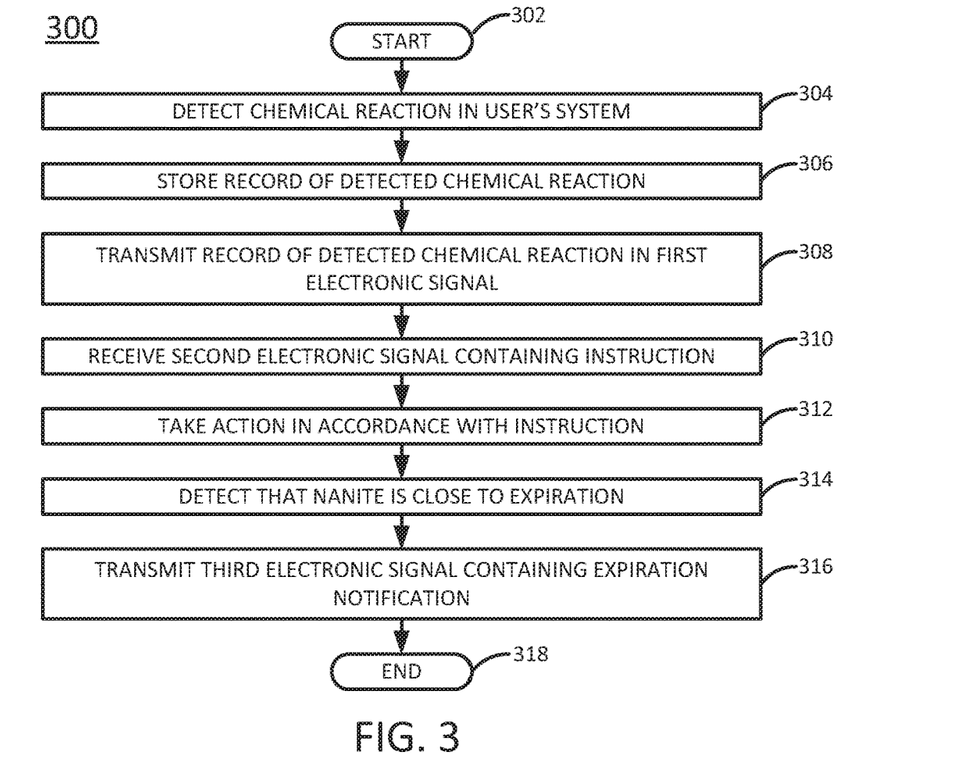
FIG. 3 illustrates a flowchart of a first example method for detecting a potential health risk.

FIG. 3 illustrates a flowchart of a first example method 300 for detecting a potential health risk. In one example, the method 300 may be performed by a nanite, e.g., one of the nanites 124, 126, 128, or 130 illustrated in FIG. 1 or the nanote 200 illustrated in FIG. 2. However, any references in the discussion of the method 300 to the nanites 124, 126, 128, or 130 of FIG. 1 or the nanite 200 of FIG. 2 are not intended to limit the means by which the method 300 may be performed.

The method 300 begins in step 302. In step 304, a nanite, having been ingested by a user, detects (e.g., via the sensor 210 of FIG. 2) a chemical reaction in the user's system. The chemical reaction may indicate that the user has been exposed to a potential health risk. In one example, the chemical reaction may be a reaction of a catalyst or enzyme with a substance (e.g., a drug or allergen) in the user's mouth. In another example, the chemical reaction may be a reaction of a catalyst or enzyme with a substance (e.g., oxygen, cholesterol, or glucose) in the user's bloodstream.

In optional step 306 (illustrated in phantom), the nanite stores a record of the detected chemical reaction (e.g., time of detection, magnitude of chemical reaction, etc.). This record may be stored in a local storage of the nanite.

In step 308, the nanite transmits (e.g., via the transceiver 212) the record of the detected chemical reaction in a first electronic signal to a user endpoint device that is within communication range of the nanite. In one example, the user endpoint device is a mobile communication device, such as a mobile phone or a wearable smart device (e.g., a smart watch or fitness tracker). For instance, the user endpoint device may be one of the UEs 108, 110, 112, or 114 illustrated in FIG. 1. In one example, the first electronic signal is transmitted using a short-range communication protocol, such as a near-field communication protocol. In a further example, a three-way handshake is used to establish a secure communication channel between the nanite and the user endpoint device before the first electronic signal is transmitted. This will protect the privacy of the information that is exchanged. Records of detected chemical reactions may be transmitted in real time upon detection (e.g., immediately upon detection, subject to any network latency), or they may be stored locally for a time and subsequently transmitted (e.g., upon request from the user endpoint device or according to a predefined transmission schedule).

In optional step 310 (illustrated in phantom), the nanite receives (e.g., via the transceiver 212) a second electronic signal from the user endpoint device. The second electronic signal may contain an instruction that instructs the nanite to take some action to counteract a potential health risk that has been detected as a result of the detected chemical reaction.

For instance, if the potential health risk is exposure to an allergen, the instruction may instruct the nanite to dispense epinephrine. If the potential health risk is exposure to lactose, the instruction may instruct the nanite to dispense lactase to break down the lactose. If the potential health risk is a high cholesterol level, the instruction may instruct the nanite to dispense a statin. If the potential health risk is a high or low blood glucose level, the instruction may instruct the nanite to dispense insulin. If the potential health risk is an open wound in a hemophiliac user, the instruction may instruct the nanite to dispense clotting factors.

In optional step 312 (illustrated in phantom), the nanite takes an action in accordance with the instruction extracted from the second electronic signal. For instance, the nanite may dispense a medication or other substance via the reservoir 206 in order to counteract a potential health risk, as discussed above.

In optional step 314 (illustrated in phantom), the nanite detects (e.g., via the sensor 210) that it is close to expiration. For instance, the nanite may detect that its supply of the detector 204 is exhausted or is close to being exhausted. The nanite may also detect that its power source 208 is low.

In optional step 316 (illustrated in phantom), the nanite transmits (e.g., via the transceiver 212) a third electronic signal to the user endpoint device. The third electronic signal contains a notification that the nanite is close to expiration. This notification will allow the user endpoint device to notify the user that it may be time to replenish his or her supply of nanites.

The method 300 ends in step 318.

Figure 4:
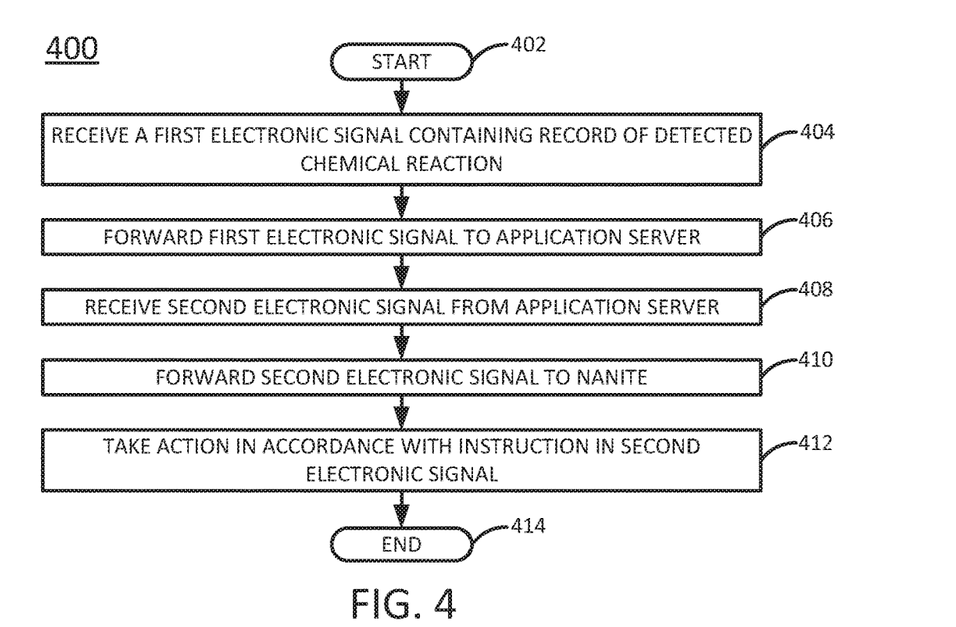
FIG. 4 illustrates a flowchart of a second example method for detecting a potential health risk.

FIG. 4 illustrates a flowchart of a second example method 400 for detecting a potential health risk. In one example, the method 400 may be performed by a mobile device such as a mobile phone or a wearable smart device, e.g., one of the user endpoint devices 108, 110, 112, or 114 illustrated in FIG. 1. However, in other examples, the method 400 may be performed by another device. As such, any references in the discussion of the method 400 to the user endpoint devices 108, 110, 112, and 114 of FIG. 1 are not intended to limit the means by which the method 400 may be performed.

The method 400 begins in step 402. In step 404, the user endpoint device receives a first electronic signal from a nanite that is deployed in the user's system or body (e.g., in the user's mouth or bloodstream). In one example, the first electronic signal contains a record of a chemical reaction detected by the nanite, where the chemical reaction may indicate exposure of the user to a potential health risk. In one example, the first electronic signal is received using a short-range communication protocol, such as a near-field communication protocol. As discussed above, a three-way handshake may be used to establish a secure communication channel between the nanite and the user endpoint device before the first electronic signal is transmitted.

In step 406, the user endpoint device forwards the first electronic signal to a remote server, such as the AS 104 illustrated in FIG. 1.

In step 408, the user endpoint device receives a second electronic signal from the remote server. The second electronic signal may contain an instruction meant to be forwarded to at least one nanite. The second electronic signal may also (or alternatively) contain an instruction meant for the user endpoint device.

In optional step 410 (illustrated in phantom), the user endpoint device forwards the second electronic signal to at least one nanite. For instance, if the second electronic signal contains an instruction that instructs the at least one nanite to take some sort of action (e.g., dispense a medication), then the user endpoint device would forward the second electronic signal to the at least one nanite so that the at least one nanite could receive the instruction and take action in a timely manner.

In optional step 412 (illustrated in phantom), the user endpoint device takes an action in accordance with the second electronic signal. For instance, the second electronic signal may contain an instruction instructing the user endpoint device to alert the user that he or she has been exposed to a potential health risk. Thus, the user endpoint device may take action by displaying a message that notifies the user of the exposure and/or advises him or her to seek further medical assistance (e.g., by checking an application for more information or visiting a doctor).

The method 400 ends in step 414.

Figure 5:
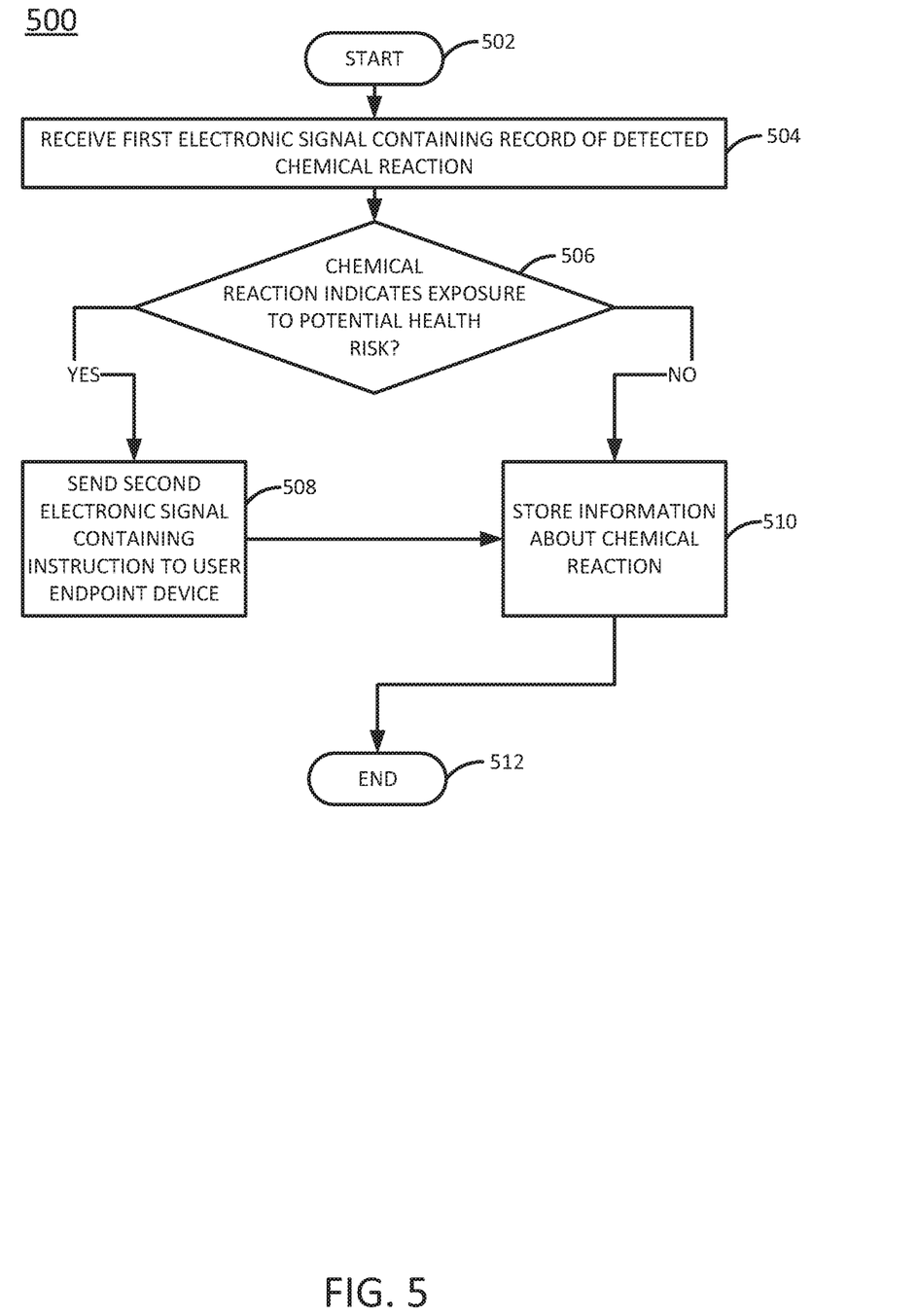
FIG. 5 illustrates a flowchart of a third example method for detecting a potential health risk.

FIG. 5 illustrates a flowchart of a third example method 500 for detecting a potential health risk. In one example, the method 500 may be performed by an application server, e.g., AS 104 illustrated in FIG. 1. However, in other examples, the method 500 may be performed by another device. As such, any references in the discussion of the method 500 to the AS 104 of FIG. 1 are not intended to limit the means by which the method 500 may be performed.

The method 500 begins in step 502. In step 504, the server receives a first electronic signal from a user endpoint device. The first electronic signal contains a record of a chemical reaction detected by nanite that is deployed in a user's system (e.g., in the user's mouth or bloodstream).

In step 506, the server determines whether the chemical reaction indicates that the user has been exposed to a potential health risk. For instance, the server may determine, based on the information in the record of the chemical reaction, whether it is more likely than not that the user's health is at risk. In one example, the determination is based on a single record of a chemical reaction (e.g., a single record indicating the presence of an allergen in the user's system or body). In another example, the determination may be based on the cumulative information contained in multiple records of chemical reactions recorded by one or more nanites in the user's system or body. For instance, the server could determine that the concentration of a particular substance (e.g., cholesterol, alcohol, glucose) in a user's bloodstream is higher than is healthy based on multiple reports of the presence of that substance over a period of time.

If the server concludes in step 506 that the user has been exposed to a potential health risk, then the method 500 proceeds to step 508. In step 508, the server sends a second electronic signal to the user endpoint device. The second electronic signal may contain an instruction meant to be forwarded to one or more nanites in the user's system (e.g., an instruction to dispense medication). The second electronic signal may also (or alternatively) contain an instruction meant for the user endpoint device (e.g., an instruction to display an alert).

In step 510, the server stores (e.g., in DB 106 of FIG. 1) information about the detected chemical reaction. The server may additionally store information about any instructions sent to nanites and/or user endpoint devices (e.g., as in step 508).

If the server concludes in step 506 that the user has not been exposed to a potential health risk, then the method 500 proceeds directly to step 510. In this case, storing the information about the detected chemical reaction may help the server to identify potential health risks in the future. For instance, this may help the server to detect when there is a spike in the concentration of a particular substance (e.g., glucose, cholesterol, etc.) in a user's bloodstream.

The method 500 ends in step 512.

Although not expressly specified above, one or more steps of the methods 300, 400, or 500 may include a storing, displaying and/or outputting step as required for a particular application. In other words, any data, records, fields, and/or intermediate results discussed in the method can be stored, displayed and/or outputted to another device as required for a particular application. Furthermore, operations, steps, or blocks in FIG. 3, 4, or 5 that recite a determining operation or involve a decision do not necessarily require that both branches of the determining operation be practiced. In other words, one of the branches of the determining operation can be deemed as an optional step. Furthermore, operations, steps or blocks of the above described method(s) can be combined, separated, and/or performed in a different order from that described above, without departing from the examples of the present disclosure.

FIG. 6 depicts a high-level block diagram of a computing device specifically programmed to perform the functions described herein. For example, any one or more components or devices illustrated in FIGS. 1 and 2 or described in connection with the methods 300, 400, or 500 may be implemented as the system 600. For instance, a nanite (such as may be used to perform the method 300), a user endpoint device (such as might be used to perform the method 400) or an application server (such as might be used to perform the method 500) could be implemented as illustrated in FIG. 6.

As depicted in FIG. 6, the system 600 comprises a hardware processor element 602, a memory 604, a module 605 for detecting potential health risks, and various input/output (I/O) devices 606.

The hardware processor 602 may comprise, for example, a microprocessor, a central processing unit (CPU), or the like. The memory 604 may comprise, for example, random access memory (RAM), read only memory (ROM), a disk drive, an optical drive, a magnetic drive, and/or a Universal Serial Bus (USB) drive. The module 605 for detecting potential health risks may include circuitry and/or logic for performing special purpose functions relating to the monitoring, analyzing, and reporting of potential health risks. The input/output devices 606 may include, for example, a camera, a video camera, storage devices (including but not limited to, a tape drive, a floppy drive, a hard disk drive or a compact disk drive), a receiver, a transmitter, a speaker, a microphone, a transducer, a display, a speech synthesizer, a haptic device, an output port, or a user input device (such as a keyboard, a keypad, a mouse, and the like).

Although only one processor element is shown, it should be noted that the general-purpose computer may employ a plurality of processor elements. Furthermore, although only one general-purpose computer is shown in the Figure, if the method(s) as discussed above is implemented in a distributed or parallel manner for a particular illustrative example, i.e., the steps of the above method(s) or the entire method(s) are implemented across multiple or parallel general-purpose computers, then the general-purpose computer of this Figure is intended to represent each of those multiple general-purpose computers. Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented.

It should be noted that the present disclosure can be implemented in software and/or in a combination of software and hardware, e.g., using application specific integrated circuits (ASIC), a programmable logic array (PLA), including a field-programmable gate array (FPGA), or a state machine deployed on a hardware device, a general purpose computer or any other hardware equivalents, e.g., computer readable instructions pertaining to the method(s) discussed above can be used to configure a hardware processor to perform the steps, functions and/or operations of the above disclosed method(s). In one example, instructions and data for the present module or process 605 for detecting potential health risks (e.g., a software program comprising computer-executable instructions) can be loaded into memory 604 and executed by hardware processor element 602 to implement the steps, functions or operations as discussed above in connection with the example methods 300, 400, or 500. Furthermore, when a hardware processor executes instructions to perform "operations," this could include the hardware processor performing the operations directly and/or facilitating, directing, or cooperating with another hardware device or component (e.g., a co-processor and the like) to perform the operations.

The processor executing the computer readable or software instructions relating to the above described method(s) can be perceived as a programmed processor or a specialized processor. As such, the present module 605 for detecting potential health risks (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. More specifically, the computer-readable storage device may comprise any physical devices that provide the ability to store information such as data and/or instructions to be accessed by a processor or a computing device such as a computer or an application server.

While various examples have been described above, it should be understood that they have been presented by way of example only, and not limitation. Thus, the breadth and scope of a preferred example should not be limited by any of the above-described example examples, but should be defined only in accordance with the following claims and their equivalents.

What is claimed is:

1. A nano-scale robotic device for deployment in a user's body, the nano-scale robotic device comprising:
   a processing system including at least one processor; and
   a non-transitory computer-readable medium storing instructions which, when executed by the processing system, cause the processing system to perform operations, operations comprising:
   releasing, from a reservoir of the nano-scale robotic device, a detector that triggers a chemical reaction upon contact with a target substance in the user's body;
   detecting when the chemical reaction occurs;
   transmitting a first electronic signal to a user endpoint device via a short-range wireless communication protocol, wherein the first electronic signal contains a record of the chemical reaction, and wherein the user endpoint device acts as an intermediary between the nano-scale robotic device and a remote server located in a core network that is accessible to the user endpoint device via a radio access network;

receiving a second electronic signal from the user endpoint device via the short-range wireless communication protocol, wherein the second electronic signal contains an instruction from the remote server to dispense a medication for treating a condition indicated by a presence of the target substance in the user's body;

detecting that a supply of the detector is close to being exhausted; and transmitting, in response to the detecting that the supply of the detector is close to being exhausted, a third electronic signal to the user endpoint device via the short-range wireless protocol, where the third electronic signal contains a notification that the nano-scale robotic device is close to expiration.

2. The nano-scale robotic device of claim 1, wherein the nano-scale robotic device is sized to be ingested into the user's body.

3. The nano-scale robotic device of claim 1, wherein the nano-scale robotic device is sized to be injected into the user's body.

4. The nano-scale robotic device of claim 1, wherein the operations further comprise:

storing energy in a power source from a renewable source of energy to power the nano-scale robotic device.

5. The nano-scale robotic device of claim 4, wherein the power source comprises a thermoelectric generator that converts heat in the user's body into the energy.

6. The nano-scale robotic device of claim 4, wherein the power source comprises a photovoltaic cell that converts infrared radiation absorbed by skin of the user's body into the energy.

7. The nano-scale robotic device of claim 4, wherein the operations further comprise:

detecting that the nano-scale robotic device is close to expiration when the energy that is stored is close to being exhausted.

8. The nano-scale robotic device of claim 1, wherein the detector is an enzyme.

9. The nano-scale robotic device of claim 1, where the detector is a catalyst.

10. The nano-scale robotic device of claim 1, wherein the operations further comprise:

storing the first electronic signal and the third electronic signal in a local memory of the nano-scale robotic device until the nano-scale robotic device is close enough to the user endpoint device to transmit the first electronic signal and the third electronic signal to the user endpoint device via the short-range wireless communication protocol.

11. The nano-scale robotic device of claim 1, wherein the nano-scale robotic device further comprises:

a shell to enclose the processing system and the non-transitory computer-readable medium; and a structure on the shell to adhere the nano-scale robotic device to a surface in the user's body.

12. A method comprising:

detecting, by a sensor of a nano-scale robotic device deployed in a user's body, when a chemical reaction is triggered by a detector released from the nano-scale robotic device coming into contact with a target substance in the user's body;

transmitting, by a transceiver of the nano-scale robotic device, a first electronic signal containing a record of the chemical reaction via a short-range wireless communication protocol to a user endpoint device, wherein the user endpoint device acts as an intermediary between the nano-scale robotic device and a remote server located in a core network that is accessible to the user endpoint device via a radio access network;

receiving, by the transceiver, a second electronic signal from the remote server via the user endpoint device, wherein the second electronic signal contains an instruction from the remote server to dispense a medication for treating a condition indicated by a presence of the target substance in the user's body;

dispensing, from a reservoir of the nano-scale robotic device, the medication;

detecting, by the sensor, when a supply of the detector is close to being exhausted; and transmitting, by the transceiver in response to the detecting that the supply of the detector is close to being exhausted, a third electronic signal to the remote server via the user endpoint device, wherein the third electronic signal contains a notification that the nano-scale robotic device is close to expiration.

13. The method of claim 12, wherein the nano-scale robotic device is sized to be ingested into the user's body.

14. The method of claim 12, wherein the nano-scale robotic device that is sized to be injected into the user's body.

15. The method of claim 12, wherein the transceiver is a short-range transceiver.

16. The method of claim 12, further comprising:

storing, by a power source of the nano-scale robotic device, energy from a renewable source of energy to power the sensor and the transceiver.

17. The method of claim 16, wherein the storing comprises:

converting heat in the user's body into the energy.

18. The method of claim 16, wherein the storing comprises:

converting infrared radiation absorbed by skin of the user's body into the energy.

19. The method of claim 12, wherein the detector is at least one selected from a group of: an enzyme and a catalyst.

20. The method of claim 12, wherein the first electronic signal, the second electronic signal, and the third electronic signal are exchanged between the nano-scale robotic device and the user endpoint device over a secure communications channel of the short-range wireless communication protocol.

* * * * *